US006970737B1

(12) United States Patent  (10) Patent No.: US 6,970,737 B1
Brodnick et al.                 (45) Date of Patent:     Nov. 29, 2005

(54) PORTABLE ECG DEVICE WITH WIRELESS COMMUNICATION INTERFACE TO REMOTELY MONITOR PATIENTS AND METHOD OF USE

(75) Inventors: Donald Eugene Brodnick, Cedarburg, WI (US); Ian Rowlandson, Fox Point, WI (US)

(73) Assignee: GE Medical Systems Information Technologies, Inc., Milwaukee, WI (US)

( * ) Notice: Subject to any disclaimer, the term of this patent is extended or adjusted under 35 U.S.C. 154(b) by 320 days.

(21) Appl. No.: 09/661,064

(22) Filed: Sep. 13, 2000

(51) Int. Cl.[7] .......................................... A61B 5/0432
(52) U.S. Cl. ............................................... 600/523
(58) Field of Search ............................... 600/508–528; 128/903, 904, 906

(56) References Cited

U.S. PATENT DOCUMENTS

| | | | |
|---|---|---|---|
| 5,544,649 A | * | 8/1996 | David et al. ................ 128/904 |
| 5,544,661 A | | 8/1996 | Davis et al. |
| 5,564,429 A | * | 10/1996 | Bornn et al. ................... 379/38 |
| 5,704,364 A | * | 1/1998 | Saltzstein et al. ............ 600/509 |
| 5,782,878 A | * | 7/1998 | Morgan et al. ............. 128/904 |
| 6,102,856 A | | 8/2000 | Groff et al. |
| 6,221,012 B1 | * | 4/2001 | Maschke et al. ............ 600/509 |
| 6,409,661 B1 | * | 6/2002 | Murphy ....................... 600/300 |

FOREIGN PATENT DOCUMENTS

| | | | |
|---|---|---|---|
| WO | WO 98/40009 | * | 9/1998 |
| WO | WO 9914882 | | 3/1999 |

OTHER PUBLICATIONS

Merriam-Webster Dictionary definitions of integrate, video, portable, television, and on-demand from m-w.com.*

* cited by examiner

Primary Examiner—George R. Evanisko
(74) Attorney, Agent, or Firm—Ziolkowski Patent Solutions Group, SC; Michael A. Della Penna; Carl B. Horton

(57) ABSTRACT

A portable ECG monitor and an overall system for remotely monitoring cardiac function of a patient is disclosed, together with a method of use. The portable ECG includes a multi-lead, multi-channel ECG monitor and a wireless communication device connected to the ECG monitor to receive patient ECG data and transmit the patient ECG data to a centralized facility, such as a hospital. The wireless communication device can include a mobile phone and/or an interactive Internet appliance. A method of remotely monitoring ECG data is also disclosed. The method and apparatus are particularly useful with patients experiencing symptomatic ischemia. The method includes providing a portable ECG device with wireless communication capabilities to such a patient, acquiring ECG data from the patient at a location remote from a health care facility, then transmitting the ECG data to the centralized facility, and assessing the ECG data at the centralized facility. The patient is then provided with instructions based on the ECG assessment. The centralized facility and the health care facility may be one in the same, or may be two different and distinct facilities.

14 Claims, 4 Drawing Sheets

PORTABLE ECG DEVICE WITH WIRELESS COMMUNICATION INTERFACE TO REMOTELY MONITOR PATIENTS AND METHOD OF USE

BACKGROUND OF THE INVENTION

The invention relates generally to electrocardiograms (ECGs) and the use thereof, and more particularly to, a method and apparatus to remotely monitor patients using a portable ECG device with a wireless communication interface.

ECG analysis is a well established method for studying the function of the heart and identifying disorders of the heart. An ECG is a graphic tracing of the variations and the electrical potential caused by the excitation of the heart muscle as detected at the body surface by the leads of the ECG device. A normal electrocardiogram is a scale or representation that shows deflections resulting from cardiac activity as changes in the magnitude of voltage and polarity over time and includes a P-Wave, a QRS complex, a T-Wave, and a U-Wave. These waves are then analyzed using a set of rules and parameters to determine what is normal and what is not. Certain deviations are used to flag possible complications.

ECG is an important tool in diagnosing patients presented to an emergency room with chest pain. One particular disorder that is studied using ECG is acute cardiac syndromes (ACS), which includes, but is not limited to, acute myocardial infarction (AMI) and acute cardiac ischemia (ACI), the latter of which is commonly referred to as unstable angina. Acute ischemia, or unstable angina, includes the starvation of oxygen to a portion of the heart, commonly caused by a partial blockage, and acute infarction is the complete blockage of oxygen to a portion of the heart. Ischemia can lead to or be a symptom of myocardial infarction. It is well known that time is critical in diagnosing these conditions in a patient experiencing chest pain.

Unstable angina, or ischemia, is sometimes difficult to diagnose and differentiate from other causes of chest pain which are not life threatening. However, since ischemia can lead to AMI, and since time to treatment is critical once AMI sets in, it is advantageous to properly diagnose an ischemic patient as soon as possible. For example, once AMI sets in, the benefit of applying treatment is reduced significantly when the elapsed time from the onset of AMI chest pain to treatment exceeds six hours. Unfortunately, patients often delay in seeking treatment when they first experience chest pain, which compromises the opportunity that exists for salvaging the heart muscles affected via treatment, such as thrombolytic therapy. Further exasperating this problem, studies have shown that patients who are under the care of a physician, and/or have previously experienced AMI, delay the most in seeking care. This may be due to the fact that the patients do not wish to "bother" the physician for "mild" pain. It may also be due to the fact that the patients may have had false alarms in the past that resulted in a long wait at the hospital.

It would therefore be advantageous if a physician, or health care provider, could supply a device to this type of patient that could expedite diagnosis and treatment by alleviating the embarrassment and time expense of showing up in an emergency department when in fact, no cardiac problem exists. This could eliminate not only the time involved in a patient going to the emergency room for indigestion, but also saves hospital resources and health insurance costs.

SUMMARY OF THE INVENTION

A method and apparatus is disclosed to remotely monitor ECG data from a patient using a portable ECG device with a wireless communication interface that solves the aforementioned problems.

In general, the invention includes the use of a multi-lead, multi-channel ECG monitor that allows 24-hour surveillance by a qualified clinician at a central facility, or hospital, of a patient experiencing symptomatic ischemia without requiring costly hospitalization. The ECG monitor is coupled with a communications device that will automatically communicate with the centralized facility, which may be a hospital, or could be a separate facility providing a specialized service to a hospital. To provide simplicity of use, the system should not require the patient to remember a phone number and require dialing the phone number when the patient is in the middle of experiencing chest pains, and preferably, there should be no extra device to plug into a wall outlet which may be time-consuming and difficult for some patients when experiencing ischemic symptoms.

Therefore, in accordance with one aspect of the invention, a portable ECG apparatus is disclosed that includes an ECG monitor connected to a plurality of lead wires and a plurality of transducers, capable of receiving a plurality of ECG signals from the patient. The ECG wireless communication device is coupled to receive patient ECG data from the ECG monitor and transmit the patient ECG data to a health care provider. The wireless communication interface can include a wireless mobile phone preconfigured to communicate directly with the health care provider and transmit voice and ECG data concurrently over a single connection. Audio communication will assist a clinician to ascertain the patient's symptoms and guide the patient in use of the device, if that is necessary. Another implementation for the wireless communication interface includes the use of an Internet appliance which has infrared communication capability to communicate with the remote ECG monitor and transmit data over the Internet. Transmission of ECG data then can also include video signals in addition to audio signals.

In accordance with another aspect of the invention, an ECG monitoring system is disclosed having a remote ECG monitor with multiple leads and multiple channels to acquire ECG signals from the patient. A remote communication and interface is coupled to the remote ECG monitor to receive the ECG signals from the remote ECG monitor and transmit the ECG signals over a public communication system to a centralized facility. A local communication interface is provided to receive the ECG signals from the public communications system at the centralized facility. A local ECG device is located in the centralized facility to connect to the local communication interface and receive the ECG signals and provide the ECG signals to a clinician or doctor in human discernable form.

In accordance with yet another aspect of the invention, a method of remotely monitoring ECG data from a patient includes providing an ECG device to a patient experiencing symptomatic ischemia for use remotely from a health care facility. The ECG device has communication capabilities to transmit ECG signals/data to a centralized facility. The method includes acquiring a multi-channel ECG from the patient at a location remote from a health care facility, transmitting the multi-channel ECG to the centralized facility, and assessing the multi-channel ECG at the centralized facility by a trained clinician or a doctor. The method also includes providing instructions to the patient based on the ECG assessment, which can include dispatching an ambulance in critical care situations. The method can also include offering remote interactive assistance in the use of the ECG device, if requested by the patient. Additionally, the patient's location can be confirmed if the patient becomes unconscious and the patient's exact location cannot be confirmed through the remote communication interface.

Various other features, objects and advantages of the present invention will be made apparent from the following detailed description and the drawings.

BRIEF DESCRIPTION OF THE DRAWINGS

The drawings illustrate one preferred embodiment presently contemplated for carrying out the invention.

In the drawings.

DETAILED DESCRIPTION OF THE PREFERRED EMBODIMENT

Figure 1:
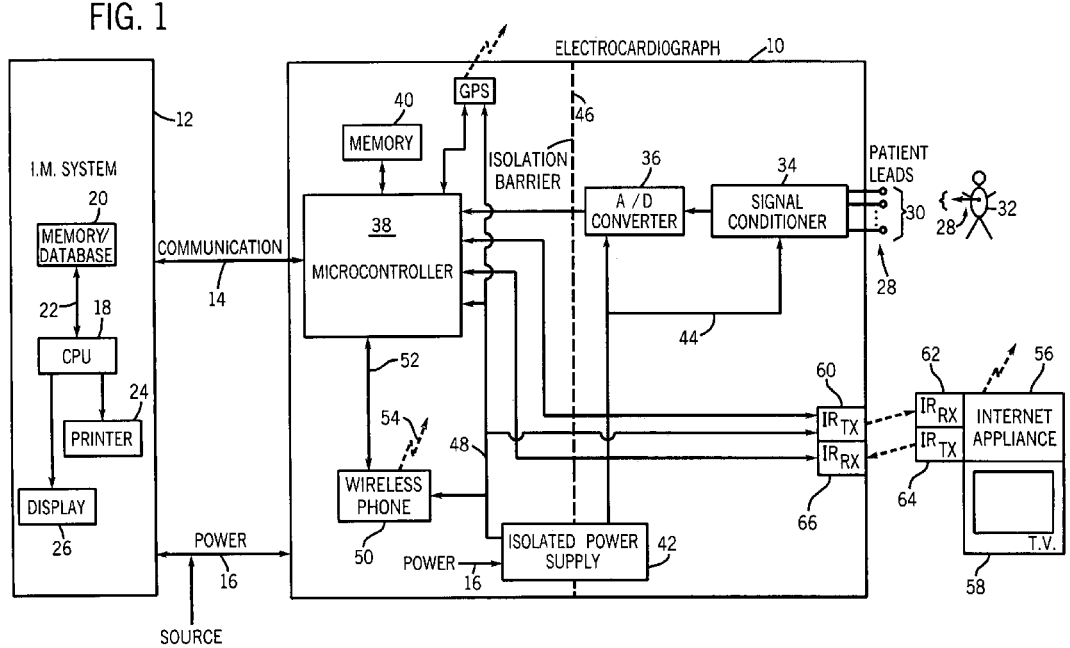
FIG. 1 is a block diagram of an electrocardiogram device incorporating the apparatus of the present invention.

Referring to FIG. 1, an electrocardiograph device 10, in accordance with the present invention, is shown optionally connected to an information management system 12 through a communications link 14. A commonly used device for acquiring an ECG is a 12-lead ECG, such as the GE Marquette MacVu or Seer-MC equipped with 12SL™. The ECG device 10 and the information management system 12 receives power 16 from an external source. Among other things, the information management system 12 includes a central processing unit 18 connected to a memory unit, or database, 20 via a data link 22. The memory unit 20 may be RAM, ROM, a mass storage unit, a floppy disk, or any other computer readable storage medium, or a combination thereof. The CPU 18 processes data and is connected to an output, such as printer 24 and/or display 26. Alternatively, the electrocardiograph 10 can be connected directly to a printer 24 or display 26 through communications link 14 if the optional information management system 12 is not utilized.

The ECG device 10 is connected to a plurality of patient lead wires 28, each having a transducer 30 to receive ECG signals from a patient 32 in a known manner. The ECG device 10 has a signal conditioner 34 that receives the ECG signals and filters noise, sets thresholds, segregates signals, and provides the appropriate number of ECG signals for the number of leads 28 to an A/D converter 36 which converts the analog signals to digital signals for processing by a microcontroller 38, or any other type of processing unit. Microcontroller 38 is connected to a memory unit 40, similar to memory unit 20, or any other computer readable storage medium. In a preferred embodiment, memory unit 40 is a combination of ROM and RAM, wherein the ROM is used for static data, such as computer programs, and the RAM is used for dynamic data, such as the ECG signals received from patient 32.

A power supply 42 is provided to supply isolated power 44 to the signal conditioner 34 and the A/D converter 36 and provide an isolation barrier 46 to isolate the lead wires 28 from un-isolated power 48 and line voltage 16. Such electrical isolation is typically provided by a medical grade isolation transformer, an optical device, or battery operation.

The ECG device 10 also includes a wireless communication device, such as wireless phone 50, which may be built into the ECG device 10, or may be an external module. The wireless phone 50 receives signals 52 from the microcontroller 38 and is capable of transmitting voice and ECG data 54 concurrently. The wireless phone 50 is powered by the uninsulated power source 48. The wireless phone may be, what is commonly known as, a cellular phone, a digital phone, or a multi-mode phone. ECG device 10 can also include an interactive Internet appliance 56 connected to a television 58, to provide interactive audio and visual communication with patient 32. The ECG device 10 includes an infrared transmitter 60 to communicate with an infrared receiver 62 of the Internet appliance 56. The Internet appliance 56 is also equipped with an infrared transmitter 64 to communicate with an infrared receiver 66 of the ECG 10. Operation of this ECG monitor system will be further described with reference to FIGS. 2–5. Alternatively, the Internet appliance 56 and television 58 can equivalently be integrated into a single unit or a personal computer with an Internet connection could equivalently serve the function of an "Internet appliance." Generally then, the "Internet appliance" is any device capable of transmitting such data over an interconnected communication system, such as the Internet.

Figure 2:
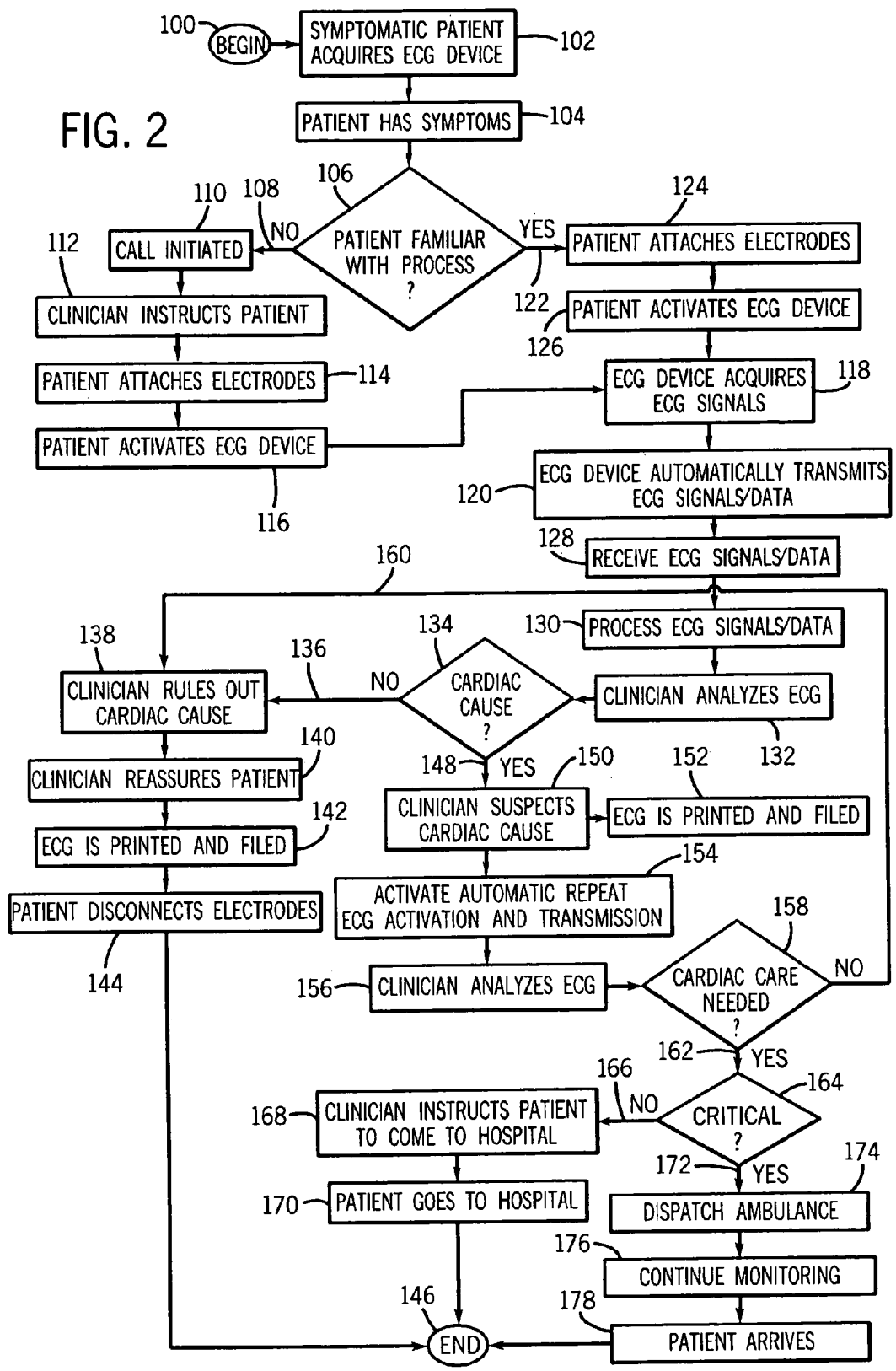
FIG. 2 is a high level flow chart depicting an algorithm at least partially incorporated into the apparatus of FIG. 1 and showing the method of the present invention.

Referring now to FIG. 2, a high level flow chart of the process 100 and use of a system incorporating the apparatus of FIG. 1 is shown. The process 100 begins with providing an ECG device, such as that described with reference to FIG. 1, to a patient experiencing symptomatic ischemia for use remotely from a health care facility 102. As will be described with further detail with reference to FIGS. 3 and 4, the ECG device includes communication capabilities to transmit raw ECG signals, or process ECG data to a centralized facility. The use of the ECG device starts when the patient experiences symptoms 104. If the patient is not familiar with using the device and the overall process 106, 108, the patient telephones the hospital 110 to acquire step by step instructions once symptoms appear. It is believed that some patients will need this service, while others will not. While all patients will receive instructions when they acquire the ECG device, it is understandable that once the patient begins to experience the symptoms of ischemia, the patient may become less likely to remember the steps and the process. Also, first time users may feel the need to be given step by step instructions by human interaction.

Once this call is initiated 110, a trained clinician will instruct the patient 112 on attaching the electrodes 114 and activating the ECG device 116. At this time the process becomes automated. The ECG signals are then acquired 118 and transmitted to the centralized facility 120. Alternatively, if the patient is familiarized with the apparatus and the process 106, 122, the patient attaches the electrodes 124 and activates the ECG device 126, which then begins to acquire the ECG signals 118 from the patient at a location remote from the health care facility. The ECG device then automatically transmits the ECG signals, or the processed ECG data 120 to the centralized facility, as will be further described with reference to FIGS. 3–5. It is noted that the ECG device can transmit either raw ECG signals to be processed later, or it can process the ECG signals and transmit the results of the multi-channel ECG.

The centralized facility then receives the ECG signals or the ECG processed data 128, and the signals/data are processed at 130. The processing can include either processing the raw ECG signals to produce a graph of the ECG, or simply decoding the transmitted processed ECG data. The trained clinician then analyzes the ECG 132, and if it is clear that there is no cardiac cause for the symptoms 134, 136, the clinician can rule out a cardiac cause for this particular episode 138. The clinician then reassures the patient 140, prints the ECG graph for the patient's file 142 and instructs the patient to disconnect the electrodes 144. The ECG device is then disabled and the process is ended at 146.

However, if the clinician suspects a cardiac cause for the symptoms the patient is experiencing 134, 148, the clinician can re-evaluate the ECG graph 150 and print the graph 152 for the patient's file while simultaneously activating an automatic repeat feature of the ECG activation and transmission at 154. The clinician then analyzes the new ECG 156 and determines if the cause is cardiac related and if care is needed 158. If the cause is determined not to be cardiac after further ECG acquisitions 158, 160, the clinician can rule out a cardiac cause 138, reassure the patient 140, print and file the ECG 142 and instruct the patient to disconnect the electrodes 144 to end the process 146. On the other hand, if the cause is determined to be cardiac related 158, 162, the clinician determines whether or not critical care is needed 164. If it is not 166, the clinician instructs the patient to go to the patient's health care facility 168. The process then concludes with the patient going to the health care facility 170, 146. Conversely, if it is determined that critical care is necessary immediately 164, 172, the centralized facility dispatches an ambulance 174 to pick up the patient and the system continues to monitor the ECG of the patient at 176 until the patient arrives at the hospital 178, which concludes the process 146.

Figure 3:
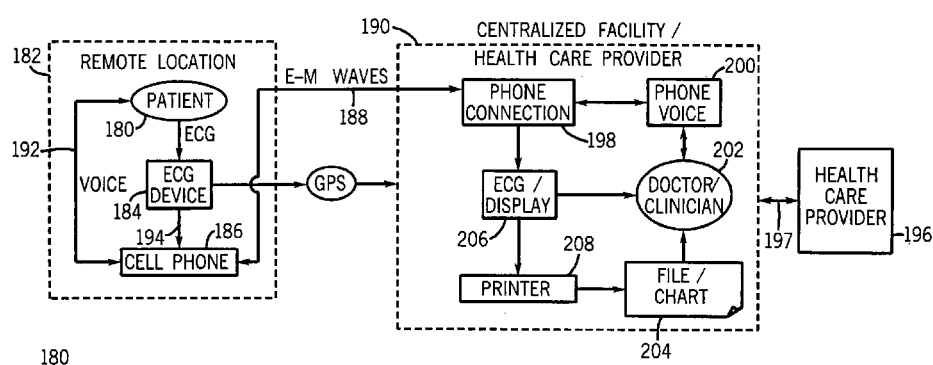
FIG. 3 is a functional block diagram of one implementation of the present invention.

FIG. 3 shows a block diagram of one embodiment of the present invention in which a patient 180 is located at a remote location 182. The patient 180 is shown connected to the portable ECG device 184, of the present invention to receive multiple channels of ECG signals from patient 180. The ECG device 184 is coupled to automatically communicate with a wireless communication device, in this case, a cellular or digital mobile phone 186. The mobile phone 186 is connected to the ECG device 184 to receive patient ECG data and to transmit the patient ECG data through electromagnetic waves 188 to a centralized health care facility 190. In this manner, both voice 192 and ECG signals 194 can be communicated in real time, or in very near real time, from the remote location 182 by electromagnetic waves 188 to the centralized health care facility 190. This transmission, occurring-over a single connection, is defined herein as being a concurrent voice and ECG data transmission. The wireless phone 186 can be constructed integral with the ECG device 184, or it can include infrared transmitter and receivers to communicate therebetween.

The centralized health care facility 190 may be a hospital, a health care provider, or a separate centralized facility providing a service of monitoring and assessing the ECG results for hospitals and health care providers and transmitting the results to the hospital or health care provider 196 through a data line 197. At the centralized facility 190, a local communication interface 198 includes a phone connection to allow voice transmissions 200 with a doctor/clinician 202, who has access to the patient's file or chart 204. The local communication interface 198 is also connected to an ECG and/or an ECG display 206 to process and/or display an ECG graph. The ECG/display 206 is connected to a printer 208 so that the ECG graph can be printed and placed in the patient's file 204. The file 204 may be an electronic chart accessible to the centralized facility 190 and/or a separate health care provider 196 via data line 197. Similarly, the doctor/clinician may communicate directly with the health care provider 196 to alert the health care provider of the results of the ECG. In accordance with the aforementioned process, the doctor/clinician 202 can talk with the patient 180 and observe the patient's ECG waveforms in real time, or in near real time, to assess the patient's condition. FIG. 3 shows one particular embodiment for dividing the functions between a centralized facility 190 and a health care provider 196, however, it is contemplated that multiple different configurations can be arranged, each of which are embodied in the appended claims.

Figure 4:
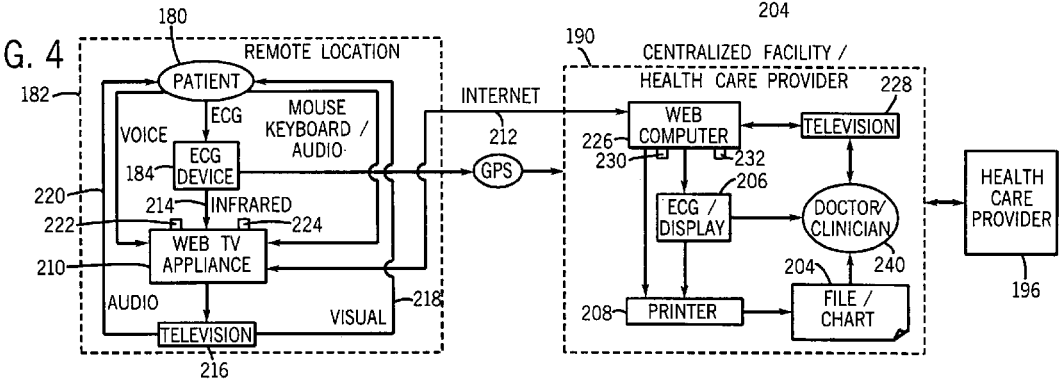
FIG. 4 is a functional block diagram of another implementation of the present invention.

Referring to FIG. 4, a second embodiment of the present invention is disclosed. Again, patient 180 is connected to the ECG device 184, of the present invention, which preferably includes a 12-channel ECG device, such as the aforementioned GE Marquette MacVu or Seer-MC equipped with 12SL™. However, in this embodiment, the wireless communication device is an interactive Internet appliance such as an interactive Internet TV appliance 210, capable of allowing voice, video and ECG data transmission through an interconnected global computer system, such as the Internet 212. The ECG device 184 and the Internet TV appliance 210 transmits data therebetween through an infrared transmission 214. Accordingly, the ECG device 184 is equipped with an infrared transmitter and the Internet TV appliance is equipped with an infrared receiver, as described with reference to FIG. 1. The Internet TV appliance 210 can also receive data instructions from the centralized facility or health care provider 190 through the Internet TV appliance 210. The Internet TV appliance 210 is connected to a television 216 to display visual signals 218 and audio signals 220 to patient 180.

Preferably, the Internet TV appliance 210 is equipped with a video camera 222 and a microphone 224 to receive and transmit audio and video signals from patient 180 to the centralized facility 190. In this manner, the processor in the ECG device 184 is programmed to allow concurrent transmission of ECG data, voice data, and video data, wherein the video and audio transmissions may be bi-directional. That is, since the voice, video, and ECG signals are communicated in real time, or near real time, from the remote location 182 to the centralized facility 190, which may be a hospital, the centralized facility 190 is thereby equipped with a Internet computer 226 that is, in turn, connected to a television 228, also equipped with a microphone 230 and a video camera 232 to transmit images and audio from a doctor or clinician 240. Similar to the embodiment of FIG. 3, the doctor or clinician at the centralized facility 190, FIG. 4, can listen to and talk to the patient 180 remotely while observing the patient's ECG waveforms. Also similar to the embodiment of FIG. 3, the ECG/display 206 receives data from the local communication interface 226. If the data has already been processed, it can go directly to the printer 208, or if the ECG of the centralized facility is processing the data, the signals go through the ECG 206, then to the printer 208. The patient's file is then updated 204.

Figure 5:
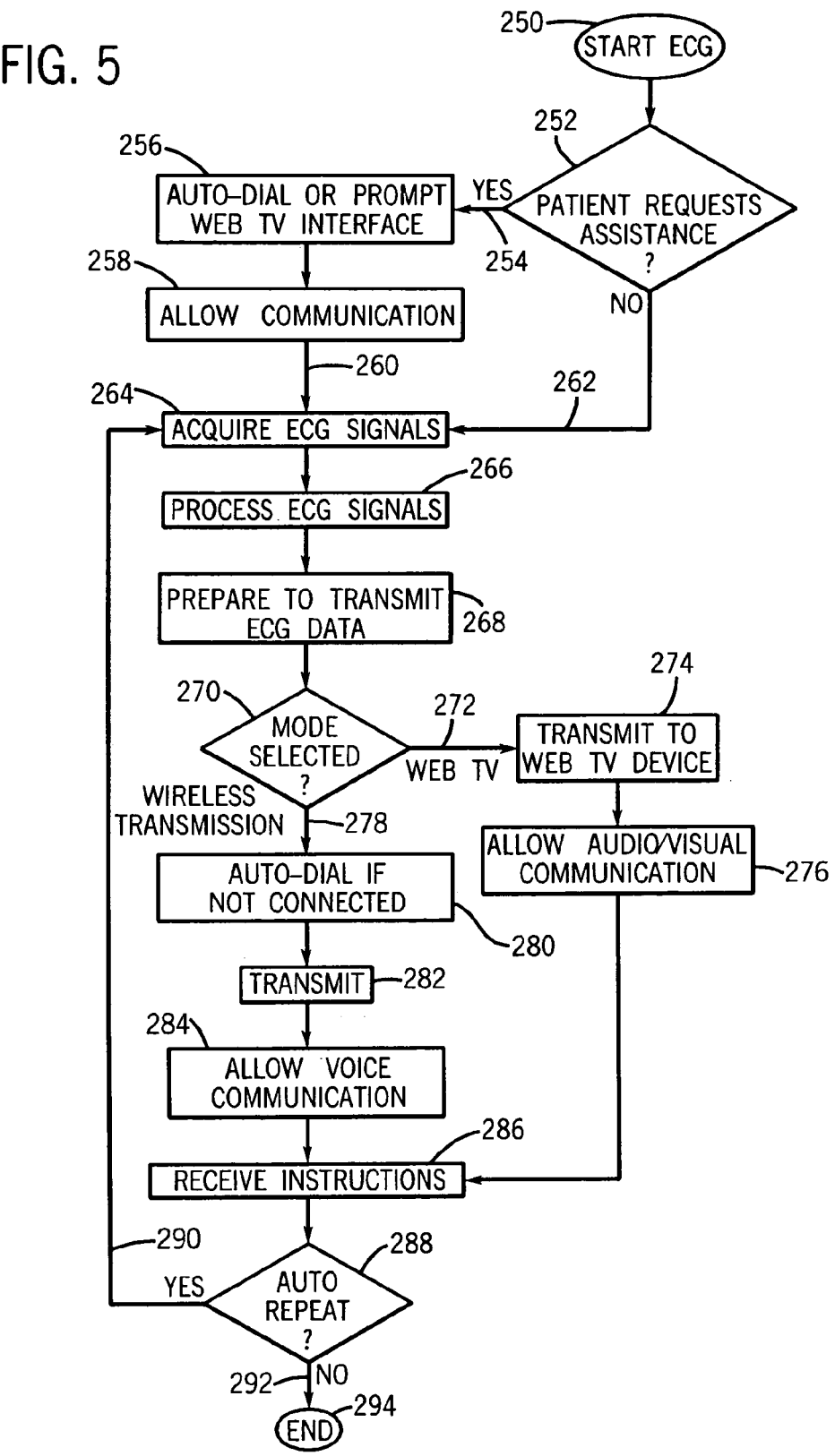
FIG. 5 is a detailed flow chart of an algorithm programmed into the electrocardiogram device of FIG. 1.

Referring to FIG. 5, a detailed flow chart of the software programmed into the portable ECG device is shown. Once the ECG is initiated 250, the program checks to see if the patient requests assistance with using the ECG device 252. If so 254, the auto-dial feature of the mobile phone is initiated or the Internet TV interface is prompted 256, at which time communication is permitted between the health care provider, or centralized facility, and the patient 258. Once the assistance is complete 260, or the patient did not require assistance 252, 262, the ECG signals are acquired 264, processed 266, and prepared for transmission at 268. The desired mode of transmission is then selected at 270 to allow concurrent transmission of ECG data and at least voice communication.

If the Internet TV mode is selected 270, 272, the ECG transmits the data to the Internet TV device 274 and allows audiovisual communication 276. Conversely, if the wireless phone transmission mode is selected 270, 278, the auto-dial feature is enabled, if not already connected 280, and the ECG transmits the data at 282, thereby allowing bi-directional voice communication 284. At this point, regardless of whether the wireless phone transmission mode is selected 278 or the Internet TV mode is selected 272, the ECG device is enabled to receive instructions 286 from the centralized facility. If the ECG is instructed to acquire more data 288, 290 the process is repeated. If not 288, 292, the ECG subroutine is complete 294.

Accordingly, the present invention includes an ECG monitoring system having a remote ECG monitor with multiple leads and multiple channels to acquire ECG signals from a patient. A remote communication interface is also provided to receive the ECG signals from the remote ECG monitor and transmit the ECG signals over a public communication system to a health care provider or centralized facility. A local communication interface is provided at the centralized facility to receive ECG signals from the public communication system and is connected to a local ECG device to receive the ECG signals and provide the ECG signals in human discernable form. The ECG signals can be processed and digitally analyzed in either the remote ECG monitor, the remote communication interface, the local communication interface, or the local ECG device. As previously discussed, the remote communication interface can either be a wireless phone or an interactive Internet appliance having a video camera or microphone to allow bi-directional communication between the patient and the health care provider. Although it may be considered redundant, an embodiment may include both.

The device can also include an information management system that includes a data link port connectable to maintain ECG monitoring during patient transport to a health care facility. The information management system can include a portable computer with data storage that is downloadable at the health care facility for recording the ECG data during transit. The information management system includes a communication system to broadcast ECG data as the patient is in transit to a health care facility.

The invention also includes a method of remotely monitoring ECG data from a patient that includes providing an ECG device to a patient experiencing symptomatic ischemia for use remotely from a health care facility. The ECG device includes the aforementioned communication capabilities to transmit ECG signals/data to a centralized facility. The method includes acquiring a multi-channel ECG from the patient at a location remote from a health care facility and transmitting the multi-channel ECG data to the centralized facility. After assessing the multi-channel ECG at the centralized facility, the method includes providing instructions to the patient based on the assessment. The method can also include offering remote interactive assistance in the use of the ECG device, if requested by the patient.

It is contemplated that the method can be conducted by a centralized facility as a service to a health care facility. That is, personnel at the centralized facility can coordinate the ECG monitoring and advise the health care facility as needed. Alternatively, the centralized facility can be integrated with the health care facility. The method also includes repeating the acquiring, transmitting, and assessing steps, as dictated by the centralized facility, or health care provider, and if an ECG assessment results in a determination that immediate medical care is needed, the method includes dispatching emergency personnel to the patient. The method can include continuing, acquiring, transmitting, and assessing the ECG while the patient is in transit to the health care facility.

With the use of an Internet TV appliance, the centralized facility can be relatively assured that the patient is located at the patient's house during use. However, the same cannot be said for the wireless phone transmission mode. In this instance, the method can include confirming a location of the patient before dispatching emergency personnel. This can be done through telephone communication, but if the patient should experience a heart attack and become unconscious, an alternative method must be provided. In this instance, the confirmation step includes receiving a GPS guidance signal from the ECG device indicative of the location of the patient. Accordingly, the ECG device optionally includes a GPS guidance system. The guidance system is initialized by the centralized facility which sends the GPS initialization signal to the ECG device, and once received, the ECG device transmits a GPS guidance signal from the ECG device to a global satellite system, which in turn transmits a location of the patient to the centralized facility.

The present invention has been described in terms of the preferred embodiment, and it is recognized that equivalents, alternatives, and modifications, aside from those expressly stated, are possible and within the scope of the appending claims.

What is claimed is:

1. An apparatus comprising:
   a lead wire assembly, each lead wire having a transducer capable of receiving an ECG signal from a patient;
   a portable ECG device including:
      a portable, ECG monitor adapted to be connected to the lead wire assembly, the ECG monitor having a data link port and a processor to process the ECG signals from the lead wire assembly and produce standard 12-lead ECG data representative of cardiac condition of the patient; and
      a wireless communication interface integrated with the ECG monitor to receive patient ECG data from the ECG monitor and transmit patient ECO data to a remote health care provider;
      an information management system connectable to the data link port of the ECG monitor to maintain ECO monitoring during patient transport to a health care facility, the information management system having data storage to maintain an ECG history that is downloadable at the health care facility; and
      wherein the processor of the portable ECG device is programmed to prompt the patient if assistance is needed to acquire an ECG, and if so, open a data transmission link to the health care provider otherwise, receive and process the ECG signals, then open a data transmission link and transmit the ECG data to the health care provider.

2. The apparatus of claim 1 wherein the wireless communication interface is a wireless phone capable of allowing audio and ECO data transmission concurrently.

3. The apparatus of claim 1 wherein the wireless communication interface is an interactive Internet TV appliance capable of allowing voice, video, and ECG data transmission concurrently.

4. The apparatus of claim 1 wherein the processor is further programmed to:
allow selection of a desired transmission mode; and
allow concurrent transmission of ECG data in addition to at least audio communication data.

5. The apparatus of claim 4 wherein the processor is further programmed to include bi-directional video and audio transmission with the transmission of ECG data.

6. The apparatus of claim 1 further comprising:
an interactive Internet appliance that is connectable to a video and audio monitor to receive ECG data from the wireless communication interface and to transmit the ECG data to the health care provider; and
a video camera and a microphone connected to the interactive Internet appliance to transmit video and audio data from the patient to the health care provider.

7. The apparatus of claim 6 wherein the apparatus is adapted to transmit the ECG data and the audio and video data to the health care provider through an interconnected global computer system.

8. The apparatus of claim 6 wherein the apparatus is adapted to transmit the ECG data and the audio and video data to the health care provider at least partially through an electromagnetic transmission wave.

9. The apparatus of claim 6 wherein the wireless communication interface includes an infrared transmitter and an infrared receiver to communicate with the interactive Internet appliance, and wherein the processor is further programmed to cause the infrared receiver to receive data instructions from the health care provider through the interactive Internet appliance.

10. The apparatus of claim 1 wherein the information management system includes a processor integral with the information management system.

11. The apparatus of claim 1 wherein the apparatus operates on demand from the patient.

12. The apparatus of claim 1 wherein the information management system is capable of broadcasting ECG data to the health care facility as the patient is in transit.

13. The apparatus of claim 1 further comprising a GPS system connected to the wireless communication interface and wherein the processor is programmed to receive a signal from the health care provider to enable the GPS system.

14. The apparatus of claim 1 wherein the information management system is operable with the processor of the ECG monitor.

* * * * *

UNITED STATES PATENT AND TRADEMARK OFFICE
CERTIFICATE OF CORRECTION

PATENT NO. : 6,970,737 B1
DATED : November 29, 2005
INVENTOR(S) : Brodnick et al.

It is certified that error appears in the above-identified patent and that said Letters Patent is hereby corrected as shown below:

Column 8,
Lines 50, 53 and 67, delete "ECO" and substitute -- ECG --.

Signed and Sealed this

Seventh Day of February, 2006

JON W. DUDAS
*Director of the United States Patent and Trademark Office*